United States Patent
Ko

(10) Patent No.: US 9,289,493 B2
(45) Date of Patent: Mar. 22, 2016

(54) METHOD FOR TREATING INFLAMMATORY CONDITIONS WITH MUCOSALLY ADMINISTERED INTERLEUKIN-2

(75) Inventor: Sai Ying Ko, Beijing (CN)

(73) Assignee: BIOLINGUS IP LLC, Hergiswil (CH)

( * ) Notice: Subject to any disclaimer, the term of this patent is extended or adjusted under 35 U.S.C. 154(b) by 0 days.

(21) Appl. No.: 13/885,993

(22) PCT Filed: Nov. 9, 2011

(86) PCT No.: PCT/AU2011/001446
§ 371 (c)(1),
(2), (4) Date: Aug. 2, 2013

(87) PCT Pub. No.: WO2012/065212
PCT Pub. Date: May 24, 2012

(65) Prior Publication Data
US 2013/0315859 A1  Nov. 28, 2013

(30) Foreign Application Priority Data

Nov. 19, 2010 (CN) .......................... 2010 1 0551433

(51) Int. Cl.
| | |
|---|---|
| *A61K 38/20* | (2006.01) |
| *A61K 9/00* | (2006.01) |
| *A61K 45/06* | (2006.01) |
| *A61K 9/16* | (2006.01) |
| *A61K 9/20* | (2006.01) |
| *A61K 9/48* | (2006.01) |

(52) U.S. Cl.
CPC ................. *A61K 45/06* (2013.01); *A61K 9/006* (2013.01); *A61K 9/0053* (2013.01); *A61K 9/0056* (2013.01); *A61K 9/1623* (2013.01); *A61K 9/2086* (2013.01); *A61K 9/4858* (2013.01); *A61K 38/20* (2013.01); *A61K 38/2013* (2013.01)

(58) Field of Classification Search
None
See application file for complete search history.

(56) References Cited

U.S. PATENT DOCUMENTS

| | | |
|---|---|---|
| 6,007,804 A | 12/1999 | Nakamura et al. |
| 2003/0135887 A1 | 7/2003 | Brandle et al. |

FOREIGN PATENT DOCUMENTS

| | | |
|---|---|---|
| EP | 1210434 B1 | 3/2008 |
| WO | 97/41831 A1 | 11/1997 |
| WO | 99/18992 | 4/1999 |
| WO | 2004/024125 | 3/2004 |
| WO | 2008/109953 | 9/2008 |

OTHER PUBLICATIONS

Banchereau, J., et al. From IL-2 to IL-37: the expanding spectrum of anti-inflammatory cytokines. Nature Immunology, 2012, vol. 13, No. 10, p. 925-931.*
Coussens, L.M. et al. Inflammation and cancer. Nature, 2002, vol. 420, p. 860-867.*
Slavin, A. et al., Mucosal administration of IL-10 enhances oral tolerance in autoimmune encephalomyelitis and diabetes, International Immunology, 2001, vol. 13, No. 6, pp. 825-833.
Sur, S. et al., Immunomodulatory effects of IL-12 on allergic lung inflammation depend on timing of doses, The Journal of Immunology, 1996, vol. 157, pp. 4173-4180.
International Search Report for PCT/AU2011/001446, dated Feb. 10, 2012.
Extended European Search Report for EP 11840904.4, dated Oct. 18, 2013.
Gariboldi et al., 2009. Low dose oral administration of cytokines for treatment of allergic asthma, Pulmon. Pharma. Therap. 22:497-510.
Pan et al., 2010. Therapeutic potential of IL-27 in systemic lupus erythematosus, Expert Opinion on Therapeutic Targets 14(5):479-484.

* cited by examiner

*Primary Examiner* — Robert Landsman
*Assistant Examiner* — Bruce D Hissong
(74) *Attorney, Agent, or Firm* — Wenderoth, Lind & Ponack, L.L.P.

(57) ABSTRACT

Provided herein are methods for the treatment of abnormal inflammation and inflammatory conditions comprising mucosal administration of an effective amount of an interleukin (e.g. IL-2) or a fragment or derivative thereof. Also provided herein are pharmaceutical compositions for mucosal administration for the treatment of abnormal inflammation and inflammatory conditions, the composition comprising said interleukin or fragment or derivative.

11 Claims, 5 Drawing Sheets

11-2009

1-2010

SEQUENCE LISTING

<160> NUMBER OF SEQ ID NOS: 3

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Homo sapiens

<400> SEQUENCE: 2

Met Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Lys Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 3
<211> LENGTH: 405
<212> TYPE: DNA

<213> ORGANISM: Homo sapiens

<400> SEQUENCE: 3

```
atgcctactt caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga aacatcttca gtgtctagaa   180
gaagaactca aacctctgaa ggaagtgcta aatttagctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt tctgaacaga   360
tggattacct tttctcaaag catcatctca acactgactt gataa                   405
```

METHOD FOR TREATING INFLAMMATORY CONDITIONS WITH MUCOSALLY ADMINISTERED INTERLEUKIN-2

TECHNICAL FIELD

The present invention relates generally to methods and compositions for use in the treatment of inflammatory conditions. Specifically the invention relates to such treatment involving the mucosal delivery of an interleukin, in particular interleukin-2 (IL-2). More particularly, the invention relates to sublingual administration of compositions comprising IL-2.

BACKGROUND ART

Inflammation is a normal and vital response mechanism assisting in protecting the body from infection and injury. However abnormal or uncontrolled inflammatory responses can result in the development of acute or chronic inflammatory disorders or conditions. Chronic inflammatory conditions can be debilitating and cause enormous discomfort and pain to sufferers. Moreover inflammatory conditions such as rheumatoid arthritis are increasing in prevalence as populations around the world age.

One fundamental failing of traditional chemically based treatments for inflammatory conditions is that these agents target only the relief of pain associated with the condition rather than addressing the underlying pathophysiology of the condition. Also associated with continued steroid use are significant side effects including stomach ulcers and bleeding. For example, non-steroidal anti-inflammatory drugs (NSAIDs) have been used for many years in anti-inflammatory therapy, however it is well known that NSAIDs produce lesions in the gastrointestinal tract depending on the length of the treatment and on the type of drug. This problem has of particular importance in cases where the therapy must be protracted for a long time, such as in the treatment of chronic inflammatory disorders including rheumatoid arthritis, where long term treatment is needed to keep the inflammatory state and associated pain under control.

Accordingly, there is a growing interest in the development of biological agent-based therapies in an effort to reduce such side effects and slow or reverse the progression of the disease.

Moreover, as most inflammatory and autoimmune diseases are chronic diseases requiring prolonged treatment, injection-based therapies and treatments requiring administration by physicians or other healthcare professionals are not ideal. Thus, the development of alternative therapies and alternative administration approaches is a focus of much research.

One biological agent that has been considered promising for the treatment of some cancers is the cytokine interleukin-2 (IL-2). A recombinant form of interleukin-2, aldesleukin (Proleukin®) has received FDA approval for the treatment of metastatic melanoma and renal cell carcinoma via injection. However to date the widespread and effective employment of IL-2 for therapeutic purposes has been considerably hampered by the significant side effects associated with its administration, due largely to the intravenous or subcutaneous delivery method required and the associated high doses necessary to achieve any therapeutic benefit via injection. Patients receiving systemic IL-2 therapy often experience flu-like symptoms. Hypotension, anaemia, and a decreased platelet count are also associated with the high cumulative doses required for intravenous administration. The most severe toxicities associated with the presently available intravenous or subcutaneous IL-2 administration result from the molecule's ability to increase capillary permeability, which may result in hypotension, ascites, generalized oedema, and pulmonary oedema. Capillary leak syndrome may ultimately lead to severely low blood pressure and reduced blood flow, heart and lung abnormalities, fluid retention, mental changes, kidney abnormalities and/or gastrointestinal abnormalities. These effects may be severe and can result in death.

The need for intravenous or subcutaneous injections of IL-2 also hampers the ability of individuals to self-medicate and manage their own treatment regime. Accordingly there is a need for the development of simple, low cost treatment options that enable sufferers of inflammatory conditions to administer their own medication with convenience and without pain or side effect.

The continued therapeutic application of IL-2 is presently being carefully assessed in light of its significant toxicity and relatively modest clinical response rate. However the present inventor has now surprisingly found, contrary to expectation, that mucosal delivery of IL-2 offers substantial therapeutic benefits over the currently available injectable delivery including the ability to achieve efficacious treatment with much reduced doses compared to those required for presently available systemic delivery. The present invention thereby provides viable new options for the cost-effective, efficacious therapeutic treatment of inflammatory conditions with reduced side effects and allowing patients to administer their own medication.

SUMMARY OF THE INVENTION

According to a first aspect the invention provides a method for the treatment of abnormal inflammation or an inflammatory condition in a subject, the method comprising mucosally administering to the subject an effective amount of an interleukin or a fragment or derivative thereof.

The interleukin may be a recombinant human interleukin. Typically the interleukin is interleukin-2 (IL-2).

Typically the mucosal administration is oral administration, more typically the administration is buccal or sublingual.

The inflammatory condition may be a chronic inflammatory disease and may be selected from, for example, arthritis such as rheumatoid arthritis, sinusitis, allergic disorders such as asthma, psoriasis, acne, inflammatory bowel diseases, chronic fatigue syndrome, autoimmune disorders such as systemic lupus erythematosus, Sjögren's syndrome, inflammation of the prostate, inflammation of the urinary tract, pancreatitis, vasculitis, diabetes, inflammation of the feet including gout, and period pain.

The interleukin may be administered in any form suitable for oral delivery, typically for sublingual or buccal delivery, such as, for example in solid or liquid unit dosage form.

The method may further comprise the administration of one or more anti-inflammatory agents. Such agents may be administered by the same route as the interleukin or via a different route. The administration of multiple agents may be sequential or concomitant.

According to a second aspect the invention provides a pharmaceutical composition for mucosal administration for the treatment of abnormal inflammation or inflammatory conditions, the composition comprising interleukin or a fragment or derivative thereof, optionally together with one or more pharmaceutically acceptable carriers, excipients and/or diluents.

According to a third aspect the invention provides a method for the treatment of abnormal inflammation or an inflammatory condition in a subject, the method comprising mucosally administering to the subject an effective amount of a composition of the second aspect.

According to a fourth aspect the invention provides the use of an interleukin or a fragment or derivative thereof for the manufacture of a medicament for treating abnormal inflammation or inflammatory conditions, wherein the medicament is administered mucosally.

Also provided is the use of an interleukin or a fragment or derivative thereof in a method for the treatment of abnormal inflammation or an inflammatory condition.

In accordance with the above aspects, the interleukin may be administered in the form of a polynucleotide encoding the interleukin. The polynucleotide may be located in a genetic construct, operably linked to a promoter.

BRIEF DESCRIPTION OF THE DRAWINGS

Embodiments of the invention are described herein, by way of example only, with reference to the accompanying drawings.

Figure 1:
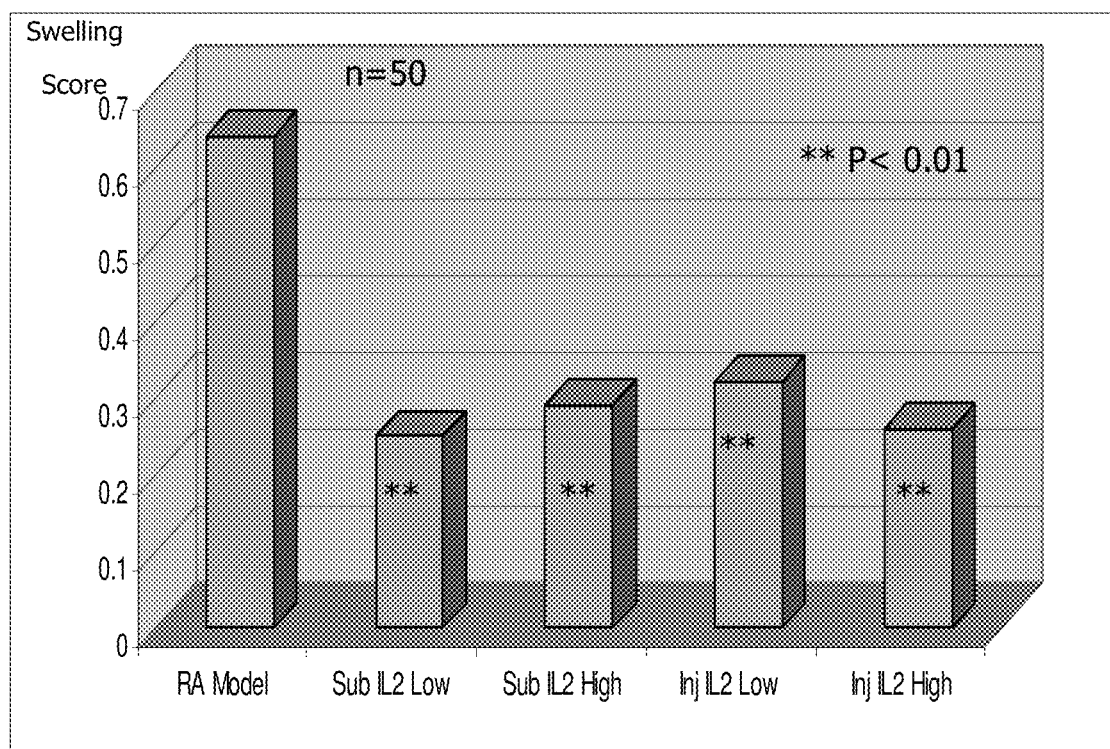
FIG. 1. Swelling (swelling score), as measured on the right hind feet of rats with induced rheumatoid arthritis, following parenteral (Inj) or sublingual (Sub) administration of recombinant human IL-2. Sublingual low dose=4000 IU/kg body weight twice daily for 7 days; sublingual high dose=12000 IU/kg body weight twice daily for 7 days; injection low dose=4000 IU/kg body weight twice daily for 7 days; injection high dose=16000 IU/kg body weight twice daily for 7 days.

Nucleotide sequences are referred to by a sequence identifier number (SEQ ID NO). The SEQ ID NOs correspond numerically to the sequence identifiers <400>1 (SEQ ID NO:1), <400>2 (SEQ ID NO:2), etc. Specifically, the amino acid sequence set forth in SEQ ID NO: 1 represents the precursor form of human IL-2, the amino acid sequence set forth in SEQ ID NO: 2 represents the mature form of human IL-2. The nucleotide sequence encoding human IL-2 is set forth in SEQ ID NO:3.

DETAILED DESCRIPTION OF THE INVENTION

Throughout this specification and the claims which follow, unless the context requires otherwise, the word "comprise", and variations such as "comprises" or "comprising", will be understood to imply the inclusion of a stated element, integer or step, or group of elements, integers or steps, but not the exclusion of any other element, integer or step, or group of elements, integers or steps.

The articles "a" and "an" are used herein to refer to one or to more than one (i.e., to at least one) of the grammatical object of the article. By way of example, "an element" means one element or more than one element.

As used herein the term "effective amount" includes within its meaning a non-toxic but sufficient amount of an agent or compound to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the terms "treating" and "treatment" refer to any and all uses which remedy a disease state or symptoms, prevent the establishment of disease, or otherwise prevent, hinder, retard, or reverse the progression of disease or other undesirable symptoms in any way whatsoever. Thus, "treatment" refers not only to treatment designed to cure or remove symptoms in an individual, but also to ongoing therapy designed to control and suppress the occurrence of symptoms. Treatment may be for a defined period of time, or provided on an ongoing basis depending on the particular circumstances of any given individual.

As used herein the term "polypeptide" means a polymer made up of amino acids linked together by peptide bonds. The terms "polypeptide" and "protein" are used interchangeably herein, although for the purposes of the present invention a "polypeptide" may constitute a portion of a full length protein. The term "polynucleotide" as used herein refers to a single- or double-stranded polymer of deoxyribonucleotide, ribonucleotide bases or known analogues or natural nucleotides, or mixtures thereof.

The present invention is predicated on the inventor's surprising findings that in in vivo models of various inflammatory conditions, sublingual administration of recombinant IL-2 results in a substantial and statistically significant therapeutic benefit without evident toxicity. Further, as exemplified herein, this mucosal administration is substantially dose independent. This is in contrast to prior art administration by injection in which higher doses are typically required to achieve similar therapeutic effect, with the dose to be administered being constrained by the generation of side effects and toxicity.

Accordingly, the present invention provides novel therapeutic treatment options for a variety of inflammatory conditions with low dosages such that side effects commonly observed with presently available systemic treatments are either obviated or reduced. To date, IL-2 therapy for the treatment of inflammatory conditions has only been attempted intravenously or subcutaneously. Such administration requires high doses of interleukin, at levels considered abnormally high relative to the levels by which cytokines such as IL-2 act to mediate cellular responses naturally. These high doses result in significant side effects to patients.

The inventor's novel finding of therapeutically efficacious mucosal interleukin administration opens the way for the development of cost effective, non toxic therapeutic alternatives to presently available injection therapies.

Accordingly, in one aspect the present invention provides a method for the treatment of an inflammatory condition in a subject, the method comprising mucosally administering to the subject an effective amount of an interleukin or a fragment or derivative thereof.

For use in accordance with the present invention the interleukin may be selected from, for example, IL-2, IL-12, IL-15 or IL-18. In particular embodiments the interleukin is IL-2, typically human IL-2, and more typically recombinant human IL-2.

The interleukin(s) used in the methods and compositions of the invention may be natural, recombinant or synthetic and may be obtained by purification from a suitable source or produced by standard recombinant DNA techniques such as those well known to persons skilled in the art, and described in, for example, Sambrook et al., *Molecular Cloning: a Laboratory Manual*, Cold Spring Harbor Laboratory Press (the disclosure of which is incorporated herein by reference). Those skilled in the art will appreciate that the precise sequence of the interleukins to be employed in accordance with the present invention may vary depending on a number of factors, for example the species and/or the inflammatory conditions to be treated. Reference to "interleukin" or "interleukins" should be understood as a reference to all forms of this molecule and to functional derivatives, variants and homologues thereof. This includes, for example, any isoforms which arise from alternative splicing of the subject interleukin mRNA or functional mutants or polymorphic variants of these proteins. Also encompassed within the scope of the invention are homologs or mimetics which possess qualitative biological activity in common with the full-length mature interleukin. Further, the present invention contemplates not only use of the interleukin polypeptide, but also polynucleotides encoding the same.

"Derivatives" of interleukins include analogues, functional fragments, parts, portions or variants from either natural or non-natural sources. Non-natural sources include, for example, recombinant or synthetic sources. By "recombinant sources" is meant that the cellular source from which the subject molecule is harvested has been genetically altered. "Analogue" means a polypeptide which is a derivative of interleukin, which derivative comprises addition, deletion, substitution of one or more amino acids, such that the polypeptide retains substantially the same function as the native interleukin from which it is derived. Modifications may be made so as to enhance the biological activity or expression level of interleukin or to otherwise increase the effectiveness of the polypeptide to achieve a desired result. The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution. Amino acid insertional derivatives also include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place.

The term "fragment" refers to a polypeptide that is a constituent of a full-length interleukin. The fragment typically possesses qualitative biological activity in common with the full-length interleukin. The fragment may be derived from the full-length interleukin polypeptide or alternatively may be synthesised by some other means, for example chemical synthesis. As used herein a "variant" of interleukin means a molecule of substantially similar sequence to the interleukin of which it is a variant and which exhibits at least some of the functional activity of the interleukin of which it is a variant. A variant may take any form and may be naturally or non-naturally occurring. Generally, variant polypeptides may share at least 25%, 30%, 35%, 40%, 45%, 50%, 55%, 60%, 65%, 70%, 75%, 80%, 85%, 90%, 95%, 96%, 97%, 98% or 99% sequence identity.

As used herein a "homologue" means that the interleukin is derived from a species other than that which is being treated in accordance with the invention. This may occur, for example, where it is determined that a species other than that which is being treated produces a form of interleukin which exhibits similar and suitable functional characteristics to that of the interleukin which is naturally produced by the subject undergoing treatment.

In accordance with a particular embodiment of the present invention, the interleukin to be administered is human IL-2 such as recombinant human IL-2. Full length human IL-2 has the amino acid sequence as set forth, in SEQ ID NO:1 (precursor form) or SEQ ID NO:2 (mature form) and in its native form is an approximately 15,500 Da glycosylated protein.

Embodiments of the present invention also provide for the administration of interleukin in the form of a polynucleotide encoding an interleukin polypeptide as described above. Typically the polynucleotide encodes human IL-2. For example an IL-2 polynucleotide of the invention may have the nucleotide sequence as set forth in SEQ ID NO:3. In addition to polynucleotides encoding the full-length human polypeptide, the invention also contemplates the use of polynucleotides encoding homologues, fragments and variants thereof.

In particular embodiments of the invention the polynucleotide may be administered in a vector. The vector may be a plasmid vector, a viral vector, or any other suitable vehicle adapted for the insertion and foreign sequences and introduction into eukaryotic cells. Typically the vector is an expression vector capable of directing the transcription of the DNA sequence of the polynucleotide encoding the desired polypeptide into mRNA. The vector may include expression control and processing sequences such as a promoter, an enhancer, ribosome binding sites, polyodenylation signals and transcription termination sequences. Examples of suitable viral expression vectors include for example Epstein-barr virus-, bovine papilloma virus-, adenovirus- and adeno-associated virus-based vectors. The vector may be episomal.

The methods and compositions of the present invention find application in the treatment of a range of inflammatory conditions including chronic inflammatory diseases. By way of example only, the inflammatory condition may be selected from arthritis such as rheumatoid arthritis, sinusitis, allergic disorders such as asthma, psoriasis, acne, inflammatory bowel diseases, chronic fatigue syndrome, autoimmune disorders such as systemic lupus erythematosus, Sjögren's syndrome, inflammation of the prostate, inflammation of the urinary tract, inflammation of the feet, pancreatitis, vasculitis, diabetes, inflammation of the feet including gout, and period pain. However, those skilled in the art will readily appreciate that the present invention is not limited to those conditions explicitly recited herein, but is applicable to the treatment of any inflammatory condition susceptible to treatment via mucosal administration of an active agent.

The present invention provides methods and compositions for the mucosal delivery of interleukin. Preferably the mucosal administration of interleukin is oral administration, although other intranasal administration, for example, inhalation, is also contemplated. Typically oral administration comprises sublingual or buccal administration whereby the composition is placed into contact with the buccal mucosa either under the tongue or in the cheek pouch allowing entry of the active agent directly to the bloodstream by absorption. Suitable forms for oral administration include solid, liquid, emulsion, gel and suspension. In a particular embodiment, a composition of the invention is administered in solid unit dosage form, for example in the form of a tablet, capsule, caplet, or lozenge. In one embodiment, the administration may comprise a gel administered to the nasal, buccal or sublingual area. In instances where the interleukin is unstable in a given liquid, this can be overcome by dissolving freeze dried interleukin powder in a diluent, for example water plus honey or carboxymethylcellulose, dextran, maltodextrin, gums, albumin, sugars such as dextrose, maltose, mannitol etc. Honey is particularly useful as it contains many antigens which may assist the interleukin immune response.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. The diluent may be dextran, dextrin, dextrose, sucrose, maltose, mannitol, gelatin, pregel starch, starch, amino acids trehalose, carboxymethylcellulose, cellulose, methyl cellulose, ethyl cellulose, albumin and propylene glycol. Typically, the carrier or carriers will form from 0.1% to 99.9% by weight of the compositions.

In particular embodiments of the present invention the interleukin, for example IL-2, is administered in the form of a solid unit dosage form such as a tablet, capsule or lozenge suitable for oral, most typically sublingual, administration. Suitable solid compositions may comprise a rapid or slow disintegrating composition comprising interleukin in a pharmaceutically acceptable water soluble or water dispersible carrier material. Such compositions may disintegrate or dissolve in the mouth upon placement under the tongue or insertion into the buccal pouch. Compositions may be formulated for rapid or immediate release of the interleukin or alternatively for delayed or controlled release. Techniques and processes for achieving delayed or controlled release of active agents are well known to those skilled in the art.

A broad range of processes for the preparation of such dosage forms are well known to those skilled in the art and are contemplated by the present invention. For example, suitable formulations may be prepared by processes including freeze drying under vacuum, supercritical fluid drying, spray drying using heat, and fluid bed spray drying. Of application in the context of particular embodiments of the present invention is a process involving microencapsulation whereby the active ingredient is coated onto granules, tablets or microparticles, typically using solvents. One particularly suitable process involves the use of a fluidised bed spray process facilitating the coating onto granules at room temperature of actives including polypeptides with a water solubilising coat, as disclosed in International Patent Application Publication No. WO 02/058735 (the disclosure of which is incorporated herein in its entirety by reference). Microparticles such as water soluble sugars or gel forming particles may be thus coated, or alternatively a blank tablet, lozenge or capsule core may be spray coated. Also known in the art are means for the preparation of oral compositions incorporating an effervescent agent as a penetration enhancer to increase the permeability of the active agent across the buccal and sublingual mucosa (see for example U.S. Pat. No. 6,974,590, the disclosure of which is incorporated herein in its entirety by reference). Other delivery modes contemplated by the present invention include the use of bioadhesives, mucoadhesives and liposomes.

The compositions of the invention may also be administered in the form of liposomes. Liposomes may be derived from phospholipids or other lipid substances, and are formed by mono- or multi-lamellar hydrated liquid crystals dispersed in aqueous medium. Specific examples of liposomes used in administering or delivering a composition to target cells are DODMA, synthetic cholesterol, DSPC, PEG-cDMA, DLinDMA, or any other non-toxic, physiologically acceptable and metabolisable lipid capable of forming liposomes. The compositions in liposome form may contain stabilisers, preservatives and/or excipients. Methods for preparing liposomes are well known in the art, for example see Methods in Cell Biology, Volume XIV, Academic Press, New York, N.Y. (1976), p. 33 ff., the contents of which are incorporated herein by reference.

The compositions of the invention may also be administered in the form of microparticles. Biodegradable microparticles formed from polylactide (PLA), polylactide-co-glycolide (PLGA), and epsilon-caprolactone ($\epsilon$-caprolactone) may be used.

The compositions of the invention may incorporate a controlled release matrix that is composed of sucrose acetate isobutyrate (SAIB) and an organic solvent or mixture of organic solvents. Polymer additives may be added to further increase the viscosity so as to decrease the release rate.

Those skilled in the art will readily appreciate that a number of suitable processes and techniques exist for the manufacture of suitable oral compositions in accordance with the present invention and that the invention is not limited by reference to any one particular process or technique.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, pregel starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth.

The therapeutically effective dose level of a composition of the present invention for any particular patient will depend upon a variety of factors including any one or more of: the type of inflammatory condition being treated and the stage of the inflammatory condition; the activity of the active agent employed; the composition employed; the age, body weight, general health, sex and diet of the patient; the time of administration; the rate of sequestration of compounds; the duration of the treatment; drugs used in combination or coincidental with the treatment, together with other related factors well known in medicine.

One skilled in the art would be able, by routine experimentation, to determine an effective, non-toxic dosage which would be required to treat applicable tumours. These will most often be determined on a case-by-case basis.

In particular embodiments of the present invention the preferred dose of interleukin, for example IL-2, is in the order of about 1 IU to about 3 million IU per day, although doses above and below this range are also contemplated. A feature of the present invention is that mucosal administration of interleukin enables significantly lower doses of interleukin to be employed than is possible with prior art approaches whilst retaining therapeutic benefit. Accordingly, the minimum dose of interleukin that may be used in accordance with the invention can be determined by those skilled in the art, provided that the dose is sufficient to achieve a therapeutic benefit. In terms of the maximum dose, this can also be determined by a person skilled in the art taking into consideration factors such as those discussed herein. For example a dose of up to several million IU per day may be appropriate in some circumstances. Typically the dose of interleukin employed in accordance with the invention is between about 1 IU and about 100,000 IU per day, between about 10 IU and about 50,000 IU per day, between about 100 IU and about 20,000 IU per day, or between about 500 IU and about 10,000 IU per day. Depending on a variety of factors as described herein, including the nature and severity of the inflammatory conditions to be treated, the daily dose administered to a patient in need thereof may be in the order of about 100 IU, 200 IU, 300 IU, 400 IU, 500 IU, 600 IU, 700 IU, 800 IU, 900 IU, 1,000 IU, 2,000 IU, 3,000 IU, 4,000 IU, 5,000 IU, 6,000 IU, 7,000 IU, 8,000 IU, 9,000 IU, 10,000 IU, 11,000 IU, 12,000 IU, 13,000 IU, 14,000 IU, 15,000 IU, 18,000 IU, 20,000 IU, 25,000 IU, 30,000 IU, 35,000 IU, 40,000 IU, 45,000 IU and about 50,000 IU.

It will also be apparent to one of ordinary skill in the art that the optimal quantity and spacing of individual dosages will be determined by the nature and extent of the inflammatory conditions being treated, the form, route and site of administration, and the nature of the particular individual being treated. Also, such optimum conditions can be determined by conventional techniques known to those skilled in the art. For example, a subject may be administered the desired daily dose in a single unit dosage form once per day, or in two unit dosage forms administered twice a day.

It will also be apparent to one of ordinary skill in the art that the optimal course of treatment, such as, the number of doses of the composition given per day for a defined number of days, can be ascertained by those skilled in the art using conventional course of treatment determination tests.

Methods and compositions of the present invention may be employed in combination with other therapies for the treatment of inflammatory conditions. For example, IL-2 may be combined with one or more additional therapeutic agents, including for example other immunomodulatory agents such as corticosteroids or other cytokines or chemokines, for example interleukins or interferon. Suitable agents which may be used in combination with the compositions of the present invention will be known to those of ordinary skill in the art.

For such combination therapies, each component of the combination may be administered at the same time, or sequentially in any order, or at different times, so as to provide the desired therapeutic effect. When administered separately, it may be preferred for the components to be administered by the same route of administration, although it is not necessary for this to be so. Alternatively, the components may be formulated together in a single dosage unit as a combination product.

All publications mentioned in this specification are herein incorporated by reference. The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It will be appreciated by persons skilled in the art that numerous variations and/or modifications may be made to the invention without departing from the spirit or scope of the invention as broadly described. The present embodiments are, therefore, to be considered in all respects as illustrative and not restrictive.

The present invention will now be further described in greater detail by reference to the following specific examples, which should not be construed as in any way limiting the scope of the invention.

EXAMPLES

Example 1

Mucosally Administered Recombinant Human IL-2 and Rheumatoid Arthritis

To determine the efficacy of mucosal administration of IL-2 in the treatment of rheumatoid arthritis, a rat model was used in which rheumatoid arthritis was induced by the administration of 0.1 ml Freund's complete adjuvant to the right hind feet of male rats (210-240 g body weight). Rat models are useful for studies of the pathogenesis of rheumatoid arthritis (RA) since rats are extraordinarily sensitive to induction of arthritis with adjuvants.

The recombinant human IL-2 was purchased from Beijing Four Rings Bio Pharmaceutical Co., Ltd. (Beijing, People's Republic of China). This was made into tablet form, each tablet containing IL-2 at 1.2 million IU per tablet and stored at 25° C. By the addition of water, the IL-2 tablets were dissolved to form a paste. Different concentrations of IL-2 as required by the experiments were then prepared by the addition of variable amounts of water prior to use. Rats were randomized into five groups of ten animals as shown in Tables 1 and 2 below. Two doses (high dose and low dose) of IL-2, as detailed in Tables 1 and 2, were administered by either intravenous injection on the tail or sublingually in tablet paste form as from day 16. Swelling in the feet of the rats was determined at days 19 and 23 following the administration of Freud's adjuvant to induce the arthritis. Swelling scores were separated according to the feet in which swelling was measured. Table 1 and FIG. 1 show the swelling score in the right hind feet of the rats (the feet in which the arthritis was induced), while Table 2 and FIG. 2 show the swelling scores ("RA index") in the remaining three feet of the rats.

Figure 2A:
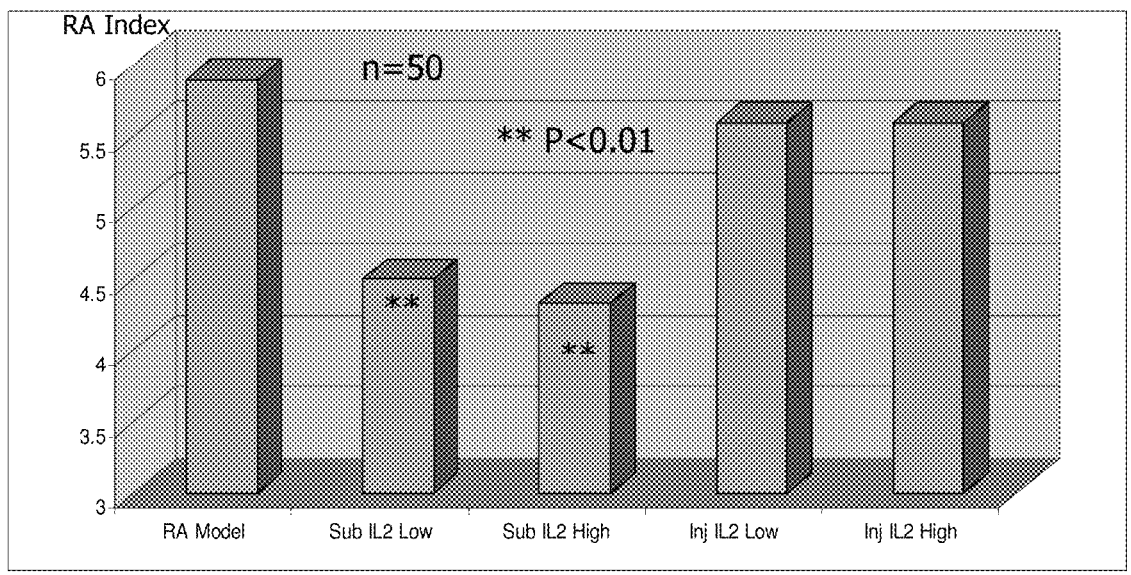
FIG. 2. Swelling (RA index), as measured on the three feet not challenged, of rats with induced rheumatoid arthritis in the right hind foot, following parenteral (Inj) or sublingual (Sub) administration of recombinant human IL-2 for 3 days (A) or 7 days (B). Sublingual low dose=4000 IU/kg body weight twice daily for 7 days; sublingual high dose=12000 IU/kg body weight twice daily for 7 days; injection low dose=4000 IU/kg body weight twice daily for 7 days; injection high dose=16000 IU/kg body weight twice daily for 7 days.
Figure 2B:
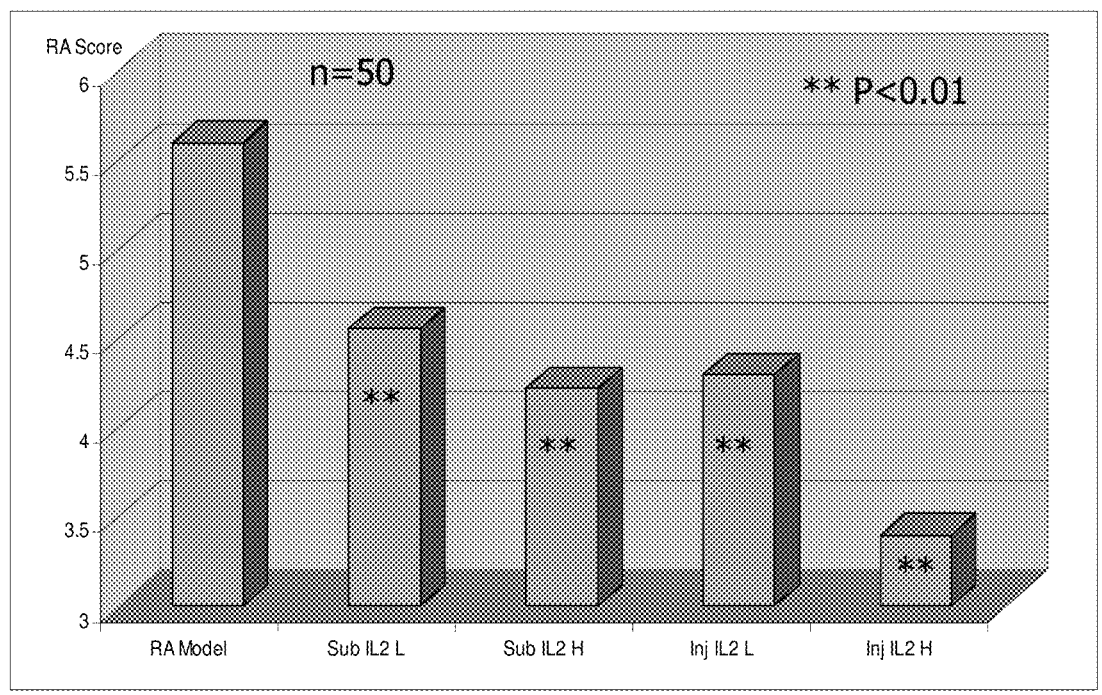

As can be seen from the tables and FIGS. 1 and 2, sublingually administered and injected IL-2 significantly reduce swelling due to rheumatoid arthritis ($p<0.01$). From the RA index (Table 2 and FIG. 2A) it can be seen that sublingual provides earlier relief (day 19) from swelling than administration by injection. No toxicity was observed in any of the treatment groups.

TABLE 1

Swelling[1] scores in rat model of rheumatoid arthritis

| Group | Treatment dose | Day 16[2] | Day 19 | Day 23[3] |
|---|---|---|---|---|
| RA model (control) | — | 0.22 ± 0.07 | 0.37 ± 0.16 | 0.64 ± 0.16 |
| Sublingual IL-2 (low) | 4000 IU/kg BW twice daily (7 days) | 0.22 ± 0.13 | 0.31 ± 0.22 | 0.25 ± 0.12** |
| Sublingual IL-2 (high) | 12000 IU/kg BW twice daily (7 days) | 0.39 ± 0.21 | 0.33 ± 0.17 | 0.29 ± 0.16** |
| IL-2 injection (low) | 4000 IU/kg BW daily (7 days) | 0.36 ± 0.18 | 0.41 ± 0.24 | 0.26 ± 0.10** |
| IL-2 injection (high) | 16000 IU/kg BW daily (7 days) | 0.35 ± 0.10 | 0.38 ± 0.17 | 0.32 ± 0.14** |

[1] = swelling on right hind foot;
[2] = dosage began;
[3] = dosage ended;
** = $p < 0.01$

TABLE 2

Swelling[1] scores in rat model of rheumatoid arthritis

| Group | Treatment dose | Day 16[2] | Day 19 | Day 23[3] |
|---|---|---|---|---|
| RA model (control) | — | 6.10 ± 0.32 | 5.90 ± 0.73 | 5.60 ± 0.70 |
| Sublingual IL-2 (low) | 4000 IU/kg BW twice daily (7 days) | 6.30 ± 0.48 | 4.50 ± 0.85** | 4.56 ± 1.13* |
| Sublingual IL-2 (high) | 12000 IU/kg BW twice daily (7 days) | 7.00 ± 0.50 | 4.33 ± 0.87** | 4.22 ± 0.67** |
| IL-2 injection (low) | 4000 IU/kg BW daily (7 days) | 6.30 ± 0.48 | 5.60 ± 0.70 | 4.30 ± 0.67** |
| IL-2 injection (high) | 16000 IU/kg BW daily (7 days) | 6.30 ± 0.67 | 5.60 ± 0.97 | 3.40 ± 0.52** |

[1] = total swelling score on three feet unchallenged;
[2] = dosage began;
[3] = dosage ended;
* = $p < 0.05$;
** = $p < 0.01$

Example 2

Sublingual Administration of Recombinant Human IL-2 and Sinusitis

Also using a rat model, the inventor also investigated the ability of sublingually administered recombinant human IL-2 to reduce the symptoms of sinusitis and reverse characteristic physiological changes induced by sinusitis. In this case sinusitis was induced in 130-150 g body weight rats by intranasal administration of 10% toluene-2,4-diisocyanate (TDI) in 10 ul olive oil daily for 7 days then every second day. Control animals received 10 ul olive oil only intranasally for the same period.

Rats were randomized into four groups of five animals as shown in Table 3 below. As detailed in Table 3, two doses (high dose and low dose) of IL-2 were administered sublingually in tablet paste form, twice daily for 14 days, beginning on day 8. Rats were sacrificed last day of the experiment (day 15 post medication) and the thymus and spleen removed for weighing.

Figure 3A:
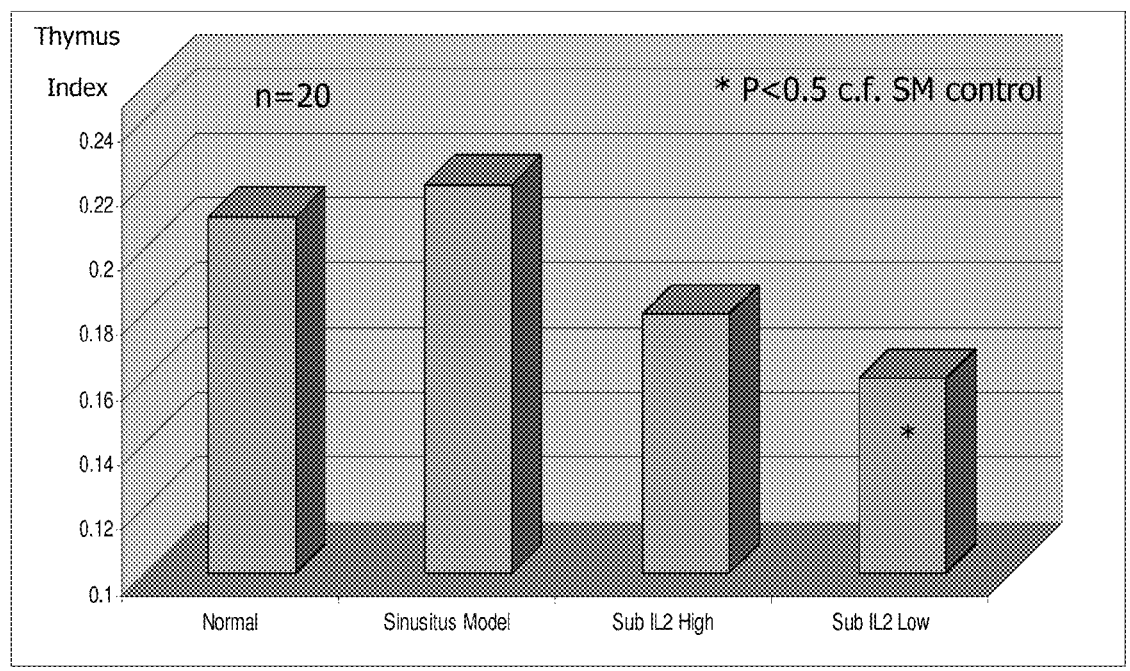
FIG. 3. Measures of sinusitis in rats with induced sinusitis following sublingual (Sub) administration of recombinant human IL-2 for 14 days. Sublingual low dose=1000 IU/kg twice daily for 7 days then every second day; sublingual high dose=4000 IU/kg twice daily for 7 days then every second day. (A) Thymus index—thymus weight (g) per 100 g body weight (B) Spleen index—spleen weight (g) per 100 g body weight.
Figure 3B:
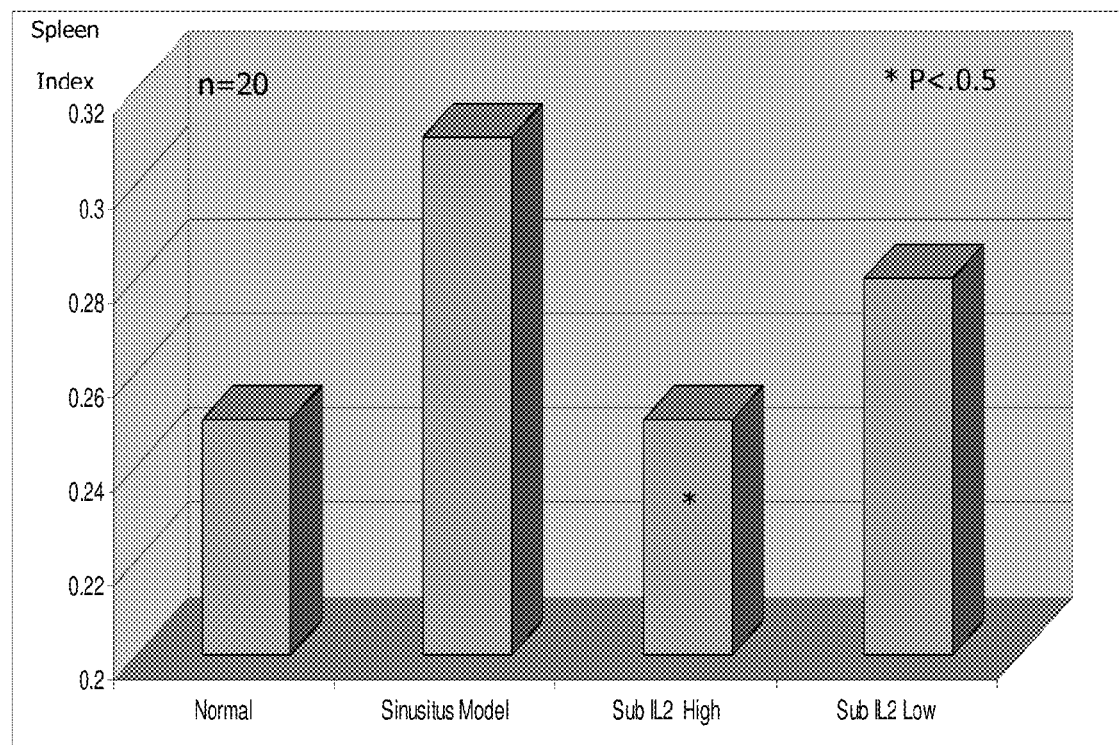

As shown in Table 3 and FIG. 3, 1000 IU IL-2 significantly ($p<0.05$) reduced the thymus index (thymus weight in g/100 g body weight) whereas 4000 IU IL-2 significantly ($p<0.05$) reduced the spleen index (spleen weight in g/100 g body weight). No toxicity was observed in any of the treatment groups.

TABLE 3

Thymus and spleen indices in a rat model of sinusitis

| Group | Body weight at end of experiment | Thymus index (g/100 g) | Spleen index (g/100 g) |
|---|---|---|---|
| Normal[1] | 292.5 ± 56.2 | 0.21 ± 0.02 | 0.25 ± 0.036 |
| Sinusitis model (control)[2] | 267.0 ± 53.2 | 0.22 ± 0.05 | 0.31 ± 0.06 |
| Sublingual IL-2 (high)[3] | 247.5 ± 52.8 | 0.18 ± 0.05 | 0.25 ± 0.04* |
| Sublingual IL-2 (low)[4] | 275.0 ± 54.5 | 0.16 ± 0.021* | 0.28 ± 0.03 |

Figure 4:
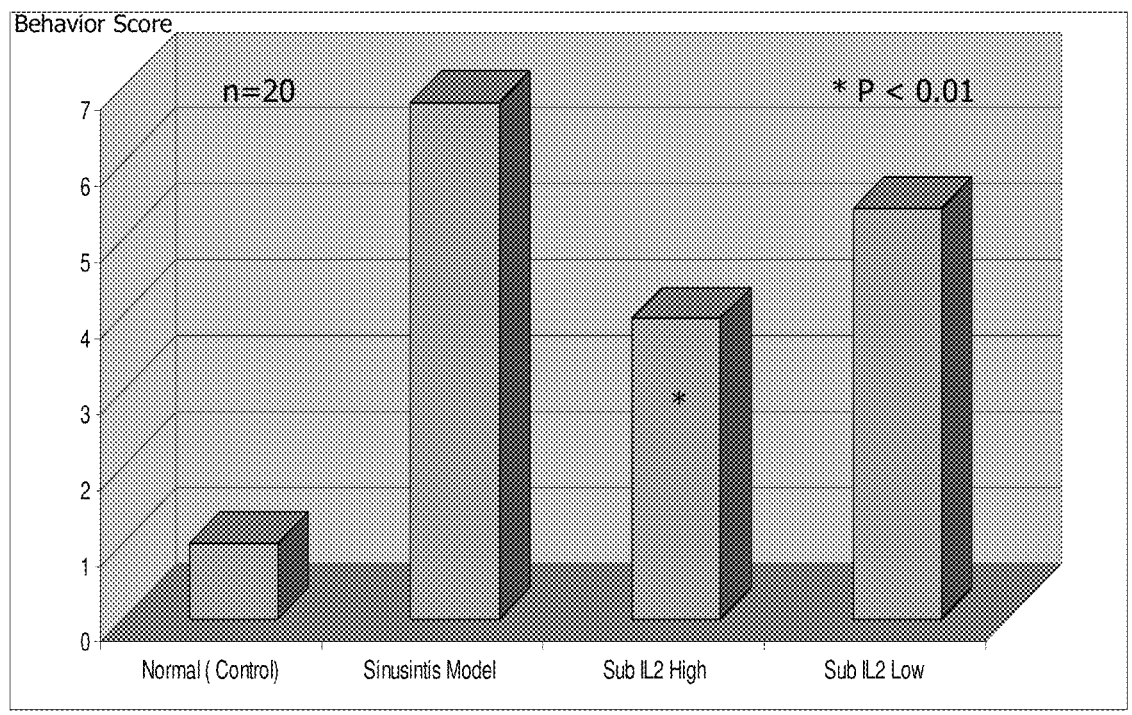
FIG. 4. Behaviour of rats with induced sinusitis following sublingual (Sub) administration of recombinant human IL-2 for 14 days, as measured by frequency of nose rubbing, sneezing and degree of nasal discharge. Sublingual low dose=1000 IU/kg twice daily for 7 days then every second day; sublingual high dose=4000 IU/kg twice daily for 7 days then every second day.

[1] = 10 ul olive oil intranasally daily for 7 days then every second day;
[2] = 10% TDI in 10 ul olive oil intranasally daily for 7 days then every second day;
[3] = 4000 IU/kg BD day 8 onwards + 10% TDI in 10 ul olive oil intranasally daily for 7 days then every second day;
[4] = 1000 IU/kg BD day 8 onwards + 10% TDI in 10 ul olive oil intranasally daily for 7 days then every second day;
* = p < 0.05 cf control Using the same treatment groups, the incidence of various behaviours associated with sinusitis were observed in the rats, specifically frequency of nose rubbing, sneezing and degree of nasal discharge. Immediately after TDI administration, behaviour variables of the rats were observed and scored for 30 minutes. A behaviour score based on a combination of the above behaviours was determined and is shown in Table 4 below at days 7, 9 and 15. As can be seen from this table and the graphical results at day 15 shown in FIG. 4, 4000 IU IL-2 significantly ($p<0.01$) reduced the observed symptoms of TDI induced sinusitis.

TABLE 4

Behaviour scores[1] in a rat model of sinusitis

| Group[2] | Treatment dose | Day 7 | Day 9 | Day 15 |
|---|---|---|---|---|
| Normal | — | 1 | 1 | 1 |
| Sinusitis model (control) | — | 6.43 | 6.8 | 6.8 |
| Sublingual IL-2 (high) | 4000 IU/kg BW twice daily | 6.45 | 4.6 | 3.95 |
| Sublingaul IL-2 (low) | 1000 IU/kg BW twice daily | 6.35 | 5.4 | 5.4 |

[1] = total score based on frequency of nose rubbing, sneezing and degree of nasal discharge;
[2] = groups as per Table 3

Example 3

Figure 5:
FIG. 5. Images showing changes in psoriasis affecting the elbow and hand of a human subject following two months administration of sublingual IL-2, 5000 IU daily.
Figure 5:
Figure 5:

Case Studies of Sublingual Administration of Recombinant Human IL-2 in Humans (i) P1: Psoriasis A human subject (P1) suffering from sever psoriasis on the elbows and back of the hands was placed on a daily regimen of 5000 IU recombinant human IL-2, administered sublingually in tablet form over a period of 2 months. The images shown in FIG. 5 clearly show the reduction in the severity and extent of the psoriasis on both the elbows and the hands of P1.

(ii) P2: Rheumatoid Arthritis

A human subject (P2) diagnosed with rheumatoid arthritis was treated with a variety of anti-inflammatory drugs over many years, including Methotrexate. After experiencing a flare up in inflammation P2 was placed on a regime of "Leflunomide" (Arava) along with the "Methotrexate" and "Mobic". The level of inflammation reduced markedly however white cell blood count dropped below the normal level necessitating a reduction in the Methotrexate from 20 to 10 mg per week and ultimately a reduction in Leflunomide from 100 to 80 mg per week. P2 was initiated on a daily regimen of 5000 IU recombinant human IL-2, administered sublingually in tablet form. P2 noticed a reduction in swelling of the hands, in particular the enlarged knuckles, and the knuckle bones are more defined. Additionally, P2 suffered from a large callous ('rheumatoid foot') on the ball of their right foot where the bones have dropped. This has been the source of a lot of discomfort and pain over many years. On a number of occasions inflammation under the callous became infected and required lancing followed by antibiotics. In 2008 P2 had x-rays of their feet and consulted 2 surgeons who recommended a surgical procedure called Dwyer interpositional (MTP) Arthroplasty, due to the destruction of the cartilage in the metatarso-phalangeal joints which led to the formation of the callous. Since taking sublingual IL-2 tablets the callous has settled down the painful underlying inflammation has subsided. The same was noticed for bunions adjacent to the big toe on each foot. They are now much less reactive and swollen. Further, after prolonged problems with crumbling teeth and the vertical fracturing of a number of roots, P2 had surgery to remove 10 teeth. The dental surgeon expressed surprise at the excellent progress of the healing following the surgery, which was attributed to the IL-2 therapy. The improvements observed with the IL-2 were observed with no obvious signs of side effect.

(iii) P3: Arthritis and Irritable Bowel Syndrome

A human subject (P3) suffered from a variety of ailments including arthritic pain, eczema and irritable bowel syndrome and received a variety of treatments for these conditions over an approximately 10 year period with variable results. P3 then began a treatment course involving a daily regimen of 5000 IU recombinant human IL-2, administered sublingually in tablet form. P3 immediately noted a reduction in all types of arthritic pain within a day of beginning the IL-2 therapy. Most significant was in the left thumb. Prior to the IL-2 treatment the base of the thumb had been painful and P3 had lost grip on the left hand due to the weakness in the thumb. Within several days of beginning the IL-2 therapy the pain had disappeared and normal functioning and use of the thumb returned. Improvements continued with the course of several months and most forms of arthritic pain disappeared or significantly subsided with no obvious signs of side effect. Over about a five month period the improvements in mobility and the reduction of arthritic symptoms were much more significant than anything previously experienced by P3, returning a level of mobility that P3 had not had for at least 17 years. Dietary precautions that P3 had previously been given have also been ignored while on, and after, the IL-2 sublingual therapy with no detriment.

For a time P3 was taking dapsone on the basis of a coeliac condition. While this was later revealed to be an incorrect diagnosis (rather the condition is irritable bowel syndrome), the dapsone effectively treated diarrhoea. This was attributed by the prescribing physician to be due to the anti-inflammatory nature of dapsone. The sublingual IL-2 therapy was able to considerably extend the period of protection that dapsone offered. Prior to the IL-2 therapy, the dosage of dapsone needed was one tablet every seven days (approximately). With the IL-2, the beneficial effect was extended to approximately ten days. Since ceasing the IL-2 therapy, P3 needed to resume taking dapsone every seven days, or less.

(iv) P4: Rheumatoid Arthritis

P4 suffered from rheumatoid arthritis for more than 20 years and used various treatments to control the inflammation including methotrexate. However P4 continued to suffer extreme pain and fatigue. Within several months of beginning sublingual therapy with 5000 IU IL-2 daily in tablet form, P4 reported dramatically reduced pain levels and no problems caused by rheumatoid arthritis.

(v) P5 Systemic Lupus Erythematosus (SLE)

P5 suffered from SLE which caused swelling on her hands, feet and some joints. Within 10 days of beginning sublingual therapy with 5000 IU IL-2 daily in tablet form, P5 reported a dramatic reduction in the swelling on her hands and feet.

Example 4

Exemplary Compositions for Treatment

In accordance with embodiments of the present invention as disclosed herein IL-2 is typically administered in the form of a pharmaceutical composition suitable for oral, most typically sublingual administration. An example of a composition in accordance with the invention is outlined below. The following is to be construed as merely an illustrative example and not as a limitation of the scope of the present invention in any way.

Example 4A

Composition for Oral Administration in Table Form

A composition comprising IL-2 in the form of a tablet may be prepared by incorporating the IL-2 into a film comprising one or more of gelatin, maltodextrin, carboxylmethyl cellulose, glucose, carbomer and coating the film onto a blank tablet core made up of known pharmaceutically acceptable ingredients selected from starch, calcium phosphates, carboxymethylethyl cellulose, mannitol, maltose, talc and magnesium stearate.

Example 4B

Composition for Oral Administration in Capsule Form

A composition comprising IL-2 in the form of a capsule may be prepared by filling a standard two-piece hard gelatin capsule with IL-2, in powdered form, 100 mg of lactose, 35 mg of talc and 10 mg of magnesium stearate.

Example 5

Pharmacokinetics of rhIL-2 Administered Sublingually to Rats

The tissue distribution of recombinant human IL-2 (rhIL-2) was determined using $^{125}$I-labelled rhIL-2 and TCA (trichloroacetic acid) precipitation assays. A single dose of 32000 IU of $^{125}$I-labelled rhIL-2 was administered sublingually to 13 male and 13 female mature, healthy Wistar rats. After administration, rats were euthanized at 10 min, 30 min, 1 hour and 3 hours and distribution of rhIL-2 in various tissues and organs determined. The lowest limit of quantitation (LLOQ) was 6 IU-equivalent/g(ml).

In descending order, $^{125}$I-labelled rhIL_2 was found in stomach, sublingual tissue, duodenum, jejunum, urione, blood serum, kidney, mandibular lymph node, submandibular gland, lymphoglandulae iliacae, pancreas, bone joints, liver, thymus, adrenal gland, celiac lymph nodes, heart, spleen and brain. Thus the highest concentrations were found in the gastrointestinal tract, sublingual tissue, urinary system, lymph nodes near the site of administration and mandibular lymph nodes. The concentration of $^{125}$I-rhIL-2 found in the brain was very low, indicative of a lack of transport of the molecule across the blood-brain barrier.

It should be noted that the radio labelled IL-2 was administered to rats in liquid form and by placing the liquid under the tongue of the rats. It is not possible to ensure that all liquid remains under the tongue of the rats such that the liquid is absorbed sublingually, and as a consequence much of the liquid is swallowed. This explains the high concentration of $^{125}$I-rhIL-2 in the gastrointestinal tract. The half life of IL-2 in serum is only 15 minutes (in humans). Thus, any IL-2 absorbed into the body will be rapidly eliminated by the kidneys. This explains the high concentration of IL-2 in urine and in the kidneys. Notwithstanding, the substantial amount of $^{125}$I-rhIL-2 in the lymph nodes demonstrates that the molecule is successfully passed through the mucosal surface into the lymphatic tissue and lymph nodes where an immune response can be initiated.

In the course of these experiments, the specific activity and immunocompetence of the radio labelled rhIL-2 was compared to that of the non radio labelled molecule and no significant difference was found (data not shown).

The invention claimed is:

1. A method for the treatment of an inflammatory condition in a subject, the method comprising mucosally administering to the subject an effective amount of interleukin-2 (IL-2), wherein the mucosal administration is sublingual administration, and wherein the inflammatory condition is selected from arthritis, sinusitis, allergic disorders, psoriasis, acne, inflammatory bowel diseases, chronic fatigue syndrome, autoimmune disorders, Sjögren's syndrome, inflammation of the prostate, inflammation of the urinary tract, pancreatitis, vasculitis, diabetes, gout or a related condition, and menstrual pain.

2. The method of claim 1 wherein the IL-2 is a recombinant IL-2.

3. The method of claim 1 wherein the inflammatory condition is a chronic inflammatory disease.

4. The method of claim 1 wherein the arthritis is rheumatoid arthritis.

5. The method of claim 1 wherein the allergic disorder is asthma.

6. The method of claim 1 wherein the autoimmune disorder is systemic lupus erythematosus.

7. The method of claim 1 wherein the IL-2 is formulated into a pharmaceutical composition comprising one or more pharmaceutically acceptable carriers, excipients or diluents.

8. The method of claim 7 wherein the pharmaceutical composition is in a solid unit dosage form.

9. The method of claim 8 wherein the solid unit dosage form comprises a tablet or capsule.

10. The method of claim 7 wherein the pharmaceutical composition is in the form of a gel.

11. The method of claim 1 further comprising the administration of one or more additional anti-inflammatory agents.

* * * * *